United States Patent
Jung

(10) Patent No.: US 9,468,394 B2
(45) Date of Patent: Oct. 18, 2016

(54) VESSEL ENCODED ARTERIAL SPIN LABELING USING FOURIER ENCODING SUITABLE FOR VASCULAR TERRITORY MAPPING

(71) Applicant: Wake Forest University Health Sciences, Winston-Salem, NC (US)

(72) Inventor: Youngkyoo Jung, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 186 days.

(21) Appl. No.: 13/780,323

(22) Filed: Feb. 28, 2013

(65) Prior Publication Data

US 2013/0231554 A1 Sep. 5, 2013

Related U.S. Application Data

(60) Provisional application No. 61/606,624, filed on Mar. 5, 2012.

(51) Int. Cl.
*A61B 5/055* (2006.01)
*G01R 33/563* (2006.01)
(Continued)

(52) U.S. Cl.
CPC ............. *A61B 5/055* (2013.01); *A61B 5/0263* (2013.01); *G01R 33/56366* (2013.01); *G06T 7/0012* (2013.01); *A61B 5/7257* (2013.01); *A61B 5/7425* (2013.01); *A61B 2576/026* (2013.01); *G01R 33/5608* (2013.01); *G06T 2207/10088* (2013.01);
(Continued)

(58) Field of Classification Search
CPC .............................. A61B 5/7257; A61B 5/055

USPC ......................................................... 600/419
See application file for complete search history.

(56) References Cited

U.S. PATENT DOCUMENTS 7,545,142 B2  6/2009  Alsop
7,587,233 B2  9/2009  Wong et al.
(Continued)

FOREIGN PATENT DOCUMENTS

EP      1 886 254 A2    2/2008
WO   WO 2006/127687 A2  11/2006
(Continued)

OTHER PUBLICATIONS

Moratal et al., k-Space tutorial: an MRI educational tool for a better understanding of k-space, 2008, Biomedical Imaging and Intervention Journal, 4(1):e15, pp. 1-8.*

(Continued)

*Primary Examiner* — Long V Le
*Assistant Examiner* — Don N Ho
(74) *Attorney, Agent, or Firm* — Myers Bigel & Sibley, P.A.

(57) ABSTRACT

Methods, systems, computer programs, circuits and workstations are configured to generate at least one two-dimensional color blood flow map that combines X and Y encoded primary and secondary peak data of 1-dimensional Inverse Fourier Transform images to visually indicate (i) anterior/posterior and right/left directional components of respective feeding arteries using defined colors and (ii) brightness to indicate an amount of blood flow associated with each voxel, with increased brightness associated with increased blood flow.

30 Claims, 10 Drawing Sheets
(6 of 10 Drawing Sheet(s) Filed in Color)

(51) Int. Cl.
  A61B 5/026  (2006.01)
  G06T 7/00   (2006.01)
  A61B 5/00   (2006.01)
  G01R 33/56  (2006.01)

(52) U.S. Cl.
  CPC .............. G06T 2207/30016 (2013.01); G06T 2207/30104 (2013.01)

(56) References Cited

U.S. PATENT DOCUMENTS

| 7,627,360 B2 | 12/2009 | Kimura |
| 7,898,254 B2 | 3/2011 | Feinberg et al. |
| 2008/0269595 A1 | 10/2008 | Wong |
| 2009/0149733 A1 | 6/2009 | Guenther |
| 2010/0240983 A1 | 9/2010 | Jung et al. |
| 2010/0274117 A1 | 10/2010 | Gunther et al. |
| 2011/0170759 A1 | 7/2011 | Bjornerud et al. |
| 2012/0243761 A1 | 9/2012 | Senzig et al. |
| 2012/0271157 A1 | 10/2012 | Wong et al. |

FOREIGN PATENT DOCUMENTS

| WO | WO 2010/108161 A2 | 9/2010 |
| WO | WO 2011/130581 A2 | 10/2011 |

OTHER PUBLICATIONS

Kansagra et al., Mapping of Vertebral Artery Perfusion Territories Using Arterial Spin Labeling MRI, 2008, Journal of Magnetic Resonance Imaging, 28, pp. 762-766.*

Jung et al., Multiphase Pseudocontinuous Arterial Spin Labeling (MP-PCASL) for Robust Quantification of Cerebral Blood Flow, 2010, Magnetic Resonance in Medicine, 64, pp. 799-810.*

Abiodun et al., MRI Reconstruction Using Discrete Fourier Transform: A tutorial, 2008, World Academy of Science, Engineering and Technology, 42, pp. 179-185.*

International Search Report and Written Opinion for related PCT Application No. PCT/US2014/020552, 14 pages, Date of mailing Jul. 7, 2014.

Kansagra et al., Improved estimation of cerebral artery branch territories using cluster-based segmentation of vessel-encoded pseudocontinuous ASL data, Proc. Intl. Soc. Mag. Reson. Med, 2012, pp. 583, vol. 20.

Alsop "ASL Perfusion Imaging: Concepts and Applications", *International Society for Magnetic Resonance in Medicine*, May 6, 2006, 5 Pages.

Chappell et al. "A General Framework for the Analysis of Vessel Encoded Arterial Spin Labeling for Vascular Territory Mapping", *Magnetic Resonance in Medicine*, 64:1529-1539, 2010.

Dai et al. "Modified pulsed continuous arterial spin labeling for labeling of a single artery", *Magnetic Resonance in Medicine*, vol. 64, No. 4, Jul. 27, 2010, pp. 975-982.

Feinberg et al. "Halving MR Imaging Time by Conjugation: Demonstration at 3.5 kG$^1$", *Radiology*, 1986; 161:527-531.

Gevers et al. "Robustness and Reproducibility of Flow Territories Defined by Planning-Free Vessel-Encoded Pseudocontinuous Arterial Spin-Labeling", *AJNR American Journal of Neuroradiology*, 33:E21-E25, Feb. 2012, Mar. 10, 2011 (Epub Ahead of Print).

International Search Report and Written Opinion Corresponding to International Application No. PCT/US2013/028919; Date of Mailing: Jun. 14, 2013; 14 Pages.

Jung "Vessel Encoded Arterial Spin Labeling using Fourier Encoding", *Proceedings of the International Society for Magnetic Resonance in Medicine*, Melbourne, Australia May 5-11, 2012, Apr. 21, 2012, p. 581.

Kansagra et al. "Quantitative Assessment of Mixed Cerebral Vascular Territory Supply With Vessel Encoded Arterial Spin Labeling MRI", *Stroke*, Aug. 14, 2008, 39:2980-2985.

Seidenwurm et al. "Performance Measures in Neuroradiology", *AJNR American Journal of Neuroradiology*, 28:1435-1438, Sep. 2007.

Tholen et al. "Suspected Carotid Artery Stenosis: Cost-effectiveness of CT Angiography in Work-up of Patients with Recent TIA or Minor Ischemic Stroke", *Radiology*, vol. 256, No. 2, Aug. 2010, pp. 585-597.

Wardlaw et al. "Non-invasive imaging compared with intra-arterial angiography in the diagnosis of symptomatic carotid stenosis: a meta-analysis", *The Lancet*, vol. 367, Issue 9521, May 6-12, 2006, pp. 1503-1512.

Wong "Vessel-Encoded Arterial Spin-Labeling Using Pseudocontinuous Tagging", *Magnetic Resonance in Medicine*, 58:1086-1091 (2007).

Wong et al. "Blind Detection of Source Vessel Locations and Resonance Offsets using Randomly Encoded VEASL", *Proc. Intl. Soc. Mag. Reson. Med.*, 19(2011), p. 294.

Wong et al. "Blind detection of vascular sources and territories using random vessel encoded arterial spin labeling", *Magnetic Resonance Materials in Physics Biology and Medicine*, 25(2):95-101, Received: Aug. 14, 2011, Published Online: Jan. 10, 2012, 7 Pages.

Wu et al. "Collateral Circulation Imaging: MR Perfusion Territory Arterial Spin-Labeling at 3T", *AJNR American Journal of Neuroradiology*, vol. 29, No. 10, Sep. 10, 2008, pp. 1855-1860.

International Preliminary Report on Patentability for PCT Application No. PCT/US2014/020552, Date of Issuance Sep. 15, 2015, 10 pages.

Essig et al., Perfusion MRI: The Five Most Frequently Asked Technical Questions, AJR Am J Roentgenol, 2013, pp. 24-34, vol. 200, No. 1.

Mohajar, Cluster analysis of the signal curves in perfusion DCE-MRI datasets, Dissertation an der Fakultat fur Statistik der Ludwig-Maximilians-Universitat Munchen, Jul. 2, 2012, 190 pages.

International Search Report and Written Opinion for corresponding PCT Application No. PCT/US2013/028919, 10 pages, Date of mailing Sep. 18, 2014.

Dai et al., Modified Pulsed Continuous Arterial Spin Labeling for Labeling of a Single Artery, Magnetic Resonance in Medicine, 2010, pp. 975-982, vol. 64.

* cited by examiner

The primary (fig. 5A) and secondary (fig. 5B) contributions from feeding arteries and a 2D color map representing the estimated locations of feeding arteries (fig. 5C). The color map was overlaid on a time-of-flight image and white circles indicate the main arteries at the tagging plane.

VESSEL ENCODED ARTERIAL SPIN LABELING USING FOURIER ENCODING SUITABLE FOR VASCULAR TERRITORY MAPPING

RELATED APPLICATIONS

This application claims the benefit of and priority to U.S. Provisional Application Ser. No. 61/606,624, filed Mar. 5, 2012, the contents of which are hereby incorporated by reference as if recited in full herein.

BACKGROUND

Carotid or vertebrobasilar stenosis restricts distal blood flow, which decreases blood supply to the parts of the brain subserved by these vessels, and increases the risk of ischemic stroke. Surgical intervention with carotid endarterectomy or endovascular angioplasty/stenting is generally pursued if the diameter of the lumen of the internal carotid artery (ICA) is reduced more than 70%, which is typically documented by noninvasive imaging. Collateral circulation increases in the brain as a normal physiologic mechanism to by-pass and compensate for the blockage in the main artery. In some cases, this increased collateral flow can supply enough oxygenated blood to maintain adequate cerebral perfusion for supporting brain function in symptom free patients. The importance of adequate hemodynamic compensation via collateral circulation has been shown in patients with cerebral arterial stenosis.

Selectively labeled blood in individual arteries can be useful for a wide range of diagnostic purposes, including monitoring disease progression in the patient with collateral circulation. Digital subtraction angiography (DSA) is considered the gold standard for assessment of collateral circulation, and is the most widely used technique. However, the procedure is invasive and requires the use of ionizing radiation, as well as the injection of iodinated contrast media. Other non-invasive methods for direct assessment of collateral circulation are MRA and transcranial doppler ultrasound.

Focal arterial stenosis can be clinically evaluated using a variety of imaging methods, including duplex ultrasound, computed tomography angiogram (CTA), and magnetic resonance angiography (MRA). Although invasive CT-based methods have been used for qualitative assessment of vascular territory perfusion, quantitative mapping of blood flow from individual source arteries is still not practical in the clinical setting. Vascular territory mapping using arterial spin labeling (ASL) has been proposed, but currently typically requires complicated planning prior to scanning and extensive post-processing, which hinders the practical clinical use of these methods. Pseudo-continuous ASL (PCASL) tagging can be used for vessel-encoded ASL (VE-ASL) utilizing gradients applied during the tagging period to spatially encode multiple feeding arteries. See, e.g., Wong, M R M, 58: 1086-1091, 2007. A random encoding strategy was introduced for the detection of arteries without a priori knowledge of vessel locations. See, Wong & Guo, 19th ISMRM: 294, 2011. However, PCASL-based VE-ASL methods often require a long scan time and complicated clustering algorithms to classify multiple vascular territories. In addition, resolving mixed signals from multiple arteries can be problematic, particularly in clinical situations where a reasonable scan time and minimal manual intervention is desired for both acquisition and post-processing.

SUMMARY OF EMBODIMENTS OF THE INVENTION

Embodiments of the invention are directed to methods, systems and circuits that can identify vascular distributions and measures of blood flow per voxel using MRI image data.

Embodiments of the invention provide systems, methods, circuits, workstations and methods suitable for automated vascular territory mapping without requiring operator intervention or complicated algorithms.

Embodiments of the invention are capable of resolving multiple sources that feed blood to a single voxel.

Embodiments of the invention may be particularly useful for MRI brain scans for evaluation of large artery diseases, cerebral vascular disease, carotid stenosis and may also be useful for stroke, especially thromboembolic stroke, and/or for evaluation of treatments or clinical trials.

Embodiments of the invention may be implemented as a routine brain scan for neurological evaluations due to the automated processing and short MRI signal acquisition time required for vascular mapping that can be provided in a color map that represents both location of source arteries (typically by a predefined different color for each artery and/or location direction) and amount of perfusion (typically in brightness and/or opacity).

Some embodiments are directed to methods of mapping brain vascular perfusion using MRI. The methods include: (a) acquiring a set of multiple pseudo-continuous arterial spin label (PCASL) images with varying phase offsets, (b) acquiring a set of pseudo-continuous arterial spin label (PCASL) images with X directional encoding; (c) acquiring a set of PCASL images with Y directional encoding; (d) electronically applying a one-dimensional inverse fourier transform (IFFT) per voxel of the X and Y encoded images; then (e) electronically evaluating each voxel of the X and Y encoded images to determine primary and secondary intensity peaks; and (f) generating at least one two-dimensional color blood flow map that combines X and Y encoded primary and secondary peak data to visually indicate anterior/posterior and right/left directional components of respective feeding arteries using defined colors and an amount of blood flow associated with each voxel using (typically scaled) brightness with increased brightness associated with increased blood flow.

The acquiring the PCASL encoded images can be carried out by first acquiring PCASL images using a sinusoidal modulation with four phase offsets to form real and imaginary parts of a complex modulation and using gradients that are in X or Y directions across an entire tagging period, and wherein the applied IFFT can resolve vessel locations in the corresponding X or Y directions.

The at least one color blood flow map can be overlaid onto a time of flight image on a display and includes visual indicia that identifies each location of four arteries at a tagging plane.

The color map can indicate the associated feeding artery per voxel in unique colors. For example, right internal carotid artery in blue, left internal carotid artery in red, and right vertebral artery in cyan, and left vertebral artery in yellow.

The generating the at least one color blood flow image can be carried out to generate a plurality of image slices that are concurrently presented in a panel or window on a display, and wherein the acquired images are non-contrast enhanced images obtained with a scan time of about 5 minutes or less.

The sinusoidal modulation can be carried out so that the sinusoidal modulation is complex with an imaginary component of the modulated signal that is 90 degrees phase offset as shown in FIG. 1 and defined below:

phase offsets ($\Delta\theta$): 0°/180° pair (for real part) and 90°/270° pair (for imaginary part)

gradient steps: $n/(\gamma \text{fov}_{det})$ n: $-(N-1)/2, \ldots, 0, \ldots, (N-1)/2$ where $\gamma$ is the gyromagnetic ratio, $\text{fov}_{det}$ is a predefined detection FOV set at the tagging plane, and N is the number of encoding steps in a direction which defines a resolution of the vessel localization.

The method can be carried out to reduce gradient steps while preserving detection resolution, so that positive or negative gradient steps are skipped and synthesized by taking the complex conjugate of the other mirrored steps based on Hermitian symmetry.

The method can include displaying the at least one map on a clinician workstation.

The acquiring steps can be carried out using a processor associated with an MR Scanner.

Other embodiments are directed to image processing circuits configured to carry out any of the above steps or features.

Some embodiments are directed to data processing circuits that include at least one processor configured to: (i) acquire set of non-contrast enhanced pseudo-continuous arterial spin label (PCASL) images with X directional encoding; (ii) acquire a set of PCASL images with Y directional encoding; (iii) apply a one-dimensional inverse fourier transform (IFFT) per voxel of the X and Y encoded images; then (iv) evaluate each voxel of the X and Y encoded images to determine primary and secondary intensity peaks; and (v) generate at least one two-dimensional color blood flow map that combines X and Y encoded primary and secondary peak data to visually indicate anterior/posterior, and right/left directional components of respective feeding arteries using defined colors and amount of blood flow associated with each voxel, with increased brightness associated with increased blood flow.

The processor (or method) can be configured to generate a series of mixing ratio color blood flow maps using a ratio of the encoded primary and secondary peak data.

Still other embodiments are directed to a computer program product having a non-transitory computer readable storage medium with computer readable program code embodied in the medium. The computer-readable program code includes: (a) computer readable program code configured to apply a one-dimensional inverse fourier transform (IFFT) per voxel of X and Y encoded pseudo-continuous arterial spin label images; (b) computer readable program code configured to evaluate each voxel of the X and Y encoded images to determine primary and secondary intensity peaks; and (c) computer readable program code configured to generate at least one two-dimensional color blood flow map that combines X and Y encoded primary and secondary peak data to visually indicate (i) anterior/posterior and right/left directional components of respective feeding arteries using defined colors and (ii) an amount of blood flow associated with each voxel, with increased brightness associated with increased blood flow.

The computer program product can also include computer readable program code configured to form the complex signal from four pseudo-continuous arterial spin label images with different phase offsets.

Other embodiments are directed to clinician workstations that include at least one display and at least one processor in communication with the at least one display. The at least one processor configured to generate at least one two-dimensional color blood flow map that combines X and Y encoded primary and secondary peak data of 1-dimensional Inverse Fourier Transform images to visually indicate (i) anterior/posterior and right/left directional components of respective feeding arteries using defined colors and (ii) an amount of blood flow associated with each voxel, with increased brightness associated with increased blood flow.

Yet other embodiments are directed to MR Scanners that include or are in communication with at least one processor configured to (i) acquire set of non-contrast pseudo-continuous arterial spin label (PCASL) images with X directional encoding and (ii) acquire a set of PCASL images with Y directional encoding.

The MR Scanner at one processor can be configured to first acquire PCASL images using a sinusoidal modulation with four phase offsets to form real and imaginary parts of a complex modulation and using gradients that are the same in X and Y directions across an entire tagging period. The sinusoidal modulation can be carried out so that the sinusoidal modulation is complex with an imaginary component of the modulated signal that is 90 degrees phase offset as shown in FIG. 1 and defined below:

phase offsets ($\Delta\theta$): 0°/180° pair (for real part) and 90°/270° pair (for imaginary part)

gradient steps: $n/(\gamma \text{fov}_{det})$ n: $-(N-1)/2, \ldots, 0, \ldots, (N-1)/2$ where $\gamma$ is the gyromagnetic ratio, $\text{fov}_{det}$ is a predefined detection FOV set at the tagging plane, and N is the number of encoding steps in a direction which defines a resolution of the vessel localization.

It is noted that aspects of the invention described with respect to one embodiment, may be incorporated in a different embodiment although not specifically described relative thereto. That is, all embodiments and/or features of any embodiment can be combined in any way and/or combination. Further, any feature or sub-feature claimed with respect to one claim may be included in another future claim without reservation and such shall be deemed supported in the claims as filed. Thus, for example, any feature claimed with respect to a method claim can be alternatively claimed as part of a system, circuit, computer readable program code or workstation. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

The foregoing and other objects and aspects of the present invention are explained in detail herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 11A is a cerebral blood flow map and FIG. 11B includes a 2D color encoded vascular territory map.

FIG. 12C is a series of 2-D images of blood mixing ratios that combine blood flow data from the secondary (FIG. 12B) and primary (FIG. 12A) encoded blood flow maps according to embodiments of the present invention.

DETAILED DESCRIPTION

Figure 1:
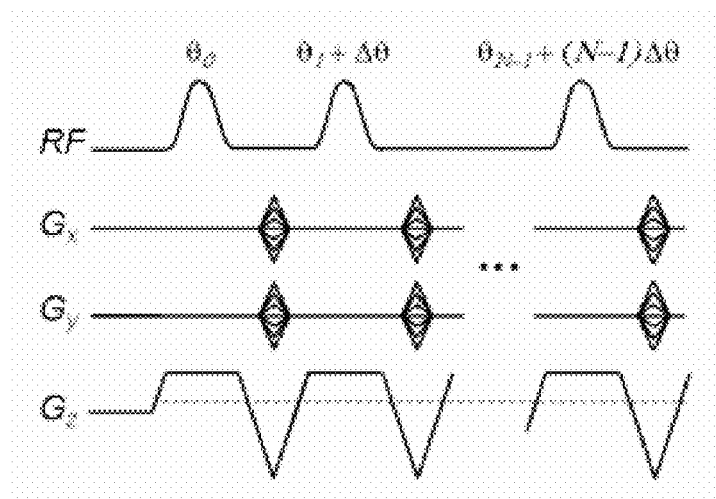
FIG. 1 is a schematic illustration of phase offsets ($\Delta\theta$) that form the real and imaginary parts of the complex modulation and same gradients in x or y are applied across the entire tagging period according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise. Features described with respect to one figure or embodiment can be associated with another embodiment of figure although not specifically described or shown as such.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

It will be understood that although the terms "first" and "second" are used herein to describe various actions, steps or components and should not be limited by these terms. These terms are only used to distinguish one action, step or component from another action, step or component. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "circuit" refers to an entirely software embodiment or an embodiment combining software and hardware aspects, features and/or components (including, for example, a processor and software associated therewith embedded therein and/or executable by, for programmatically directing and/or performing certain described actions or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MRI scanner" or MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: Signa 1.5T/3.0T; Philips Medical Systems: Achieva 1.5T/3.0T; Integra 1.5T; Siemens: MAGNETOM Avanto; MAGNETOM Espree; MAGNETOM Symphony; MAGNETOM Trio; and MAGNETOM Verio. As is well known, the MR scanner can include a main operating/control system that is housed in one or more cabinets that reside in an MR control room while the MRI magnet resides in the MR scan suite. The control room and scan room can be referred to as an MR suite and the two rooms can be separated by an RF shield wall. The term "high-magnetic field" refers to field strengths above about 0.5 T, typically above 1.0T, and more typically between about 1.5T and 10T. Embodiments of the invention may be particularly suitable for 1.5T, 2.0T and 3.0T systems, or higher field systems such as future contemplated systems at 4.0T, 5.0T, 6.0T and the like. The methods and systems can also be applied to animal MRI data acquired from animal MRI scanners. The term "patient" refers to humans and animals.

The term "automatically" and derivatives thereof means that the operation and/or method can be substantially, and typically entirely, carried out without manual input, and is typically programmatically directed and/or carried out. The term "electronically" with respect to connections includes both wireless and wired connections between components.

The term "clinician" means physician, neurologist, radiologist, physicist, or other medical personnel desiring to review medical data of a patient. The term "workstation" refers to a display and/or computer associated with a clinician.

The term "reconstruction" is used broadly to refer to original or post-acquisition and storage and subsequent construction of image slices or images of an image data set.

Each article, reference and patent cited or discussed herein is hereby incorporated by reference as if recited in full herein.

It is also noted, for clarity, that while certain of the figures are described as "color" or "color-coded" (or color-encoded), these terms refer to a defined unique color or color scale of pixels/voxels correlated to source artery location and/or blood flow direction to illustrate vessel (e.g., source artery) and blood flow direction. The color map can have both x and y directional modulation so that a user can visually ascertain which source artery and/or direction the source artery is located for particular perfusion regions. The color map can indicate the associated feeding artery per voxel in unique colors. For example, right internal carotid artery in blue, left internal carotid artery in red, and right vertebral artery in cyan, and left vertebral artery in yellow. Thus, for example, in x direction modulation, a first color, such as blue, represents that the source artery is to the left while a second color, such as red, indicates that the source artery is to the left. One color, e.g., red, can refer to "from anterior" and another color, e.g., yellow, can refer to "from posterior" in y directional modulation. The color-coded map can also be configured to illustrate an amount of perfusion by a scale of brightness such that brightness indicates intensity of each voxel that is proportional to blood flow for a respective voxel. Also, to comply with filing rules, black and white copies or grey scale versions of these images may be used in support of the application.

The term "about" refers to a parameter that can vary from the recited value, typically between +/−20%. For time parameters in minutes or hours, for example, the stated value includes times that are +/−5 minutes of that number.

The term "time of flight" (TOF) refers to MRI angiography that is based on the phenomenon of flow-related enhancement of spins entering into an imaging slice. As a result of being unsaturated, these spins can give more signal that surrounding stationary spins.

As noted above, PCASL-based VE-ASL methods often require long scan times and complicated clustering algorithms to classify multiple vascular territories. Embodiments of the invention are configured to perform VE-ASL by encoding blood signal in the Fourier space based on the source location.

Generally stated, embodiments of the invention are configured to use Fourier encoding for quantitative vascular territory mapping without requiring any prior knowledge of accurate locations of feeding arteries or any complicated post processing algorithms. In addition, embodiments of the invention employ image processing methods that are resistant if not immune to phase errors due to resonance offsets and can be performed within clinically relevant scan time typically about 5 minutes or less. In some embodiments includes an MRI active scanning time that is less than 5 minutes for a particular patient session.

Embodiments of the invention are directed to techniques for vessel encoded ASL using Fourier encoding PCASL. The PCASL acquisition includes multiple phase offsets. The tagging efficiency, a signal difference of tag/control pair, can roughly be represented as a sinusoidal function and is modulated by the offset phase of the tagging RF pulses. The conventional PCASL acquires images with 0 and 180 degrees phase offsets and subtracted each other to get tagged blood signal. The phase offset used by embodiments of the present invention is represented in FIG. 1 as $\Delta\theta$. The conventional pair becomes the real part of a complex sinusoidal modulation. The sinusoidal modulation should be complex and the imaginary component of the modulated signal can be formulated with additional pair with 90 and 270 degree phase offsets. Embodiments of the invention can include four PCASL acquisitions, which are repeated with varying phase offsets: i.e., phase offsets ($\Delta\theta$): 0°/180° pair (for real part) and 90°/270° pair (for imaginary part).

FIG. 1 illustrates four phase offsets ($\Delta\theta$) form the real and imaginary parts of the complex modulation and the same gradients in x or y are applied across the entire tagging period. Multiple gradient steps allow the Fourier encoding to resolve vessel locations in x or y direction. The phase offsets ($\Delta\theta$) can be 0°/180° pair (for the "real" part) and 90°/270° pair (for the "imaginary" part).

The PCASL acquisition can include a plurality of spatial modulation steps. Gradient pulses between tagging RF pulses define the periodicity (or wave length) of the sinusoidal modulation based on the location of a feeding artery. When multiple gradient steps (gradient steps in x and y gradients shown in FIG. 1) are applied, like phase encoding steps in imaging:

gradient steps: $n/(\gamma fov_{det})$ n: $-(N-1)/2, \ldots, 0, \ldots, (N-1)/2$ Where $\gamma$ is the gyromagnetic ratio, $fov_{det}$ is the predefined detection FOV set at the tagging plane, and N is the number of encoding steps in a direction. The number of steps (N) defines the resolution of the vessel localization.

The example shown in FIG. 2 has 15 steps in the x gradient direction and 9 steps in the y gradient direction, i.e., the procedure forming the complex signal shown above can be repeated 15 times in x directional encoding and 9 times in y directional encoding. Other numbers of directional encoding can be used in either direction and the same number can be used in each direction.

FIG. 1 shows the four phase offsets ($\Delta\theta$) form the real and imaginary parts of the complex modulation and same gradients in x or y are applied across the entire tagging period. Multiple gradient steps allow the Fourier encoding to resolve vessel locations in x or y direction.

The 1D inverse Fourier transform converts the modulated complex signal into the projected ASL signals onto the encoding direction. Note that taking the absolute value of the Fourier transformed signal removes the phase errors due to off-resonance effects at the location of the artery. When the acquisition and processing are performed in two orthogonal directions, such as physical x and y axes, the vessel location in 2D space can be estimated. In addition, an analysis of multiple peaks in x and/or y directional encoding allow detection of multiple sources since arterial mixing, if present, can be expressed as the superposition of each sinusoid.

To reduce the gradient steps while preserving the detection resolution, positive or negative gradient steps can be omitted and synthesized by taking the complex conjugate of the other mirrored steps based on Hermitian symmetry. When the Hermitian symmetry is applied, the phase component of DC signal, which is acquired without gradient encoding, is removed through all acquired data and the synthesis is performed. As will be understood by one of skill in the art, Hermitian symmetry is from a simple mathematical concept, which means if any signal is real, not complex, then its frequency signal, which is the inverse transform of the real signal, meets the Hermitian symmetry. Therefore, the removal of DC signal phase, which is identical no matter in spatial domain or frequency domain, allows the assumption that the inverse Fourier transformed signal is real.

In embodiments of the application, the use of this concept is primarily intended for 1D, an early implementation of this theory in MRI was first proposed by for use in 2D by Feinberg et al. See, Fienberg et al., *Halving MR Imaging Time by Conjugation: Demonstration at 3.5 kg*, Radiology 1986; 161: 527-531, the contents of which are hereby incorporated by reference as if recited in full herein.

Figure 2A:
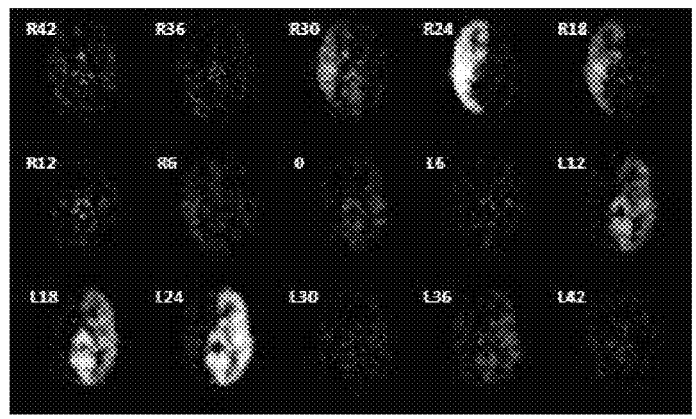
FIGS. 2A and 2B are a series of inverse Fourier transformed images representing feed arteries in x (FIG. 2A) and y (FIG. 2B) directions. The labels at the upper left corners indicate the estimated locations of source arteries.
Figure 2B:
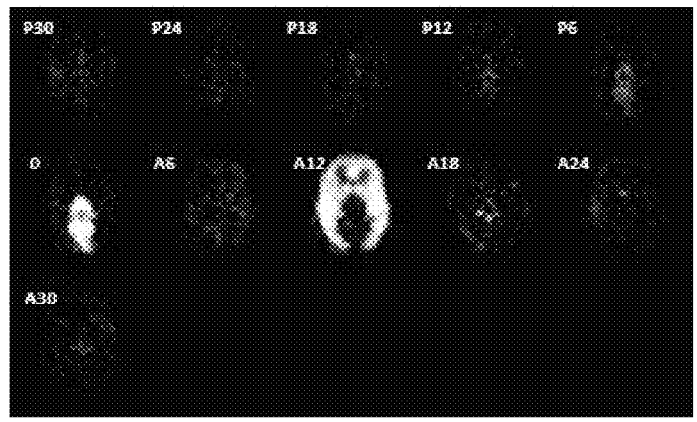

An Inverse Fourier Transform (IFFT) can be carried out for localization of one or more feeding arteries. The location of the source artery can be detected after applying the inverse Fourier transform through images with multiple gradient modulation steps. The 1D inverse Fourier transform converts the modulated complex signal into the projected ASL signals onto the encoding direction, X or Y. FIGS. 2A/2B shows examples of inverse Fourier transformed images where the intensities indicate the detected location in X (FIG. 2A) and Y (FIG. 2B) directions. In FIGS. 2A/2B, the inverse Fourier transformed images show the location of feeding arteries in X (FIG. 2A) and Y (FIG. 2B) directions with labels at the upper left corners indicating the estimated locations of the source arteries. The locations of primary (highest intensity) and secondary (the second highest intensity) peaks can be determined. An electronic search of maximum intensity and correlation of the physical location (in 2D or 3D space) of the maximum intensity can represent the amount blood flow and the location of a primary perfusion component. The detection of a second highest peak can give information of a secondary component when mixing is present. FIGS. 2A/2B show single slice vessel encoded images across x and y directions. The peak locations of an individual voxel in two orthogonal directions can allow estimates of a 2D location of the source artery.

Figure 3A:
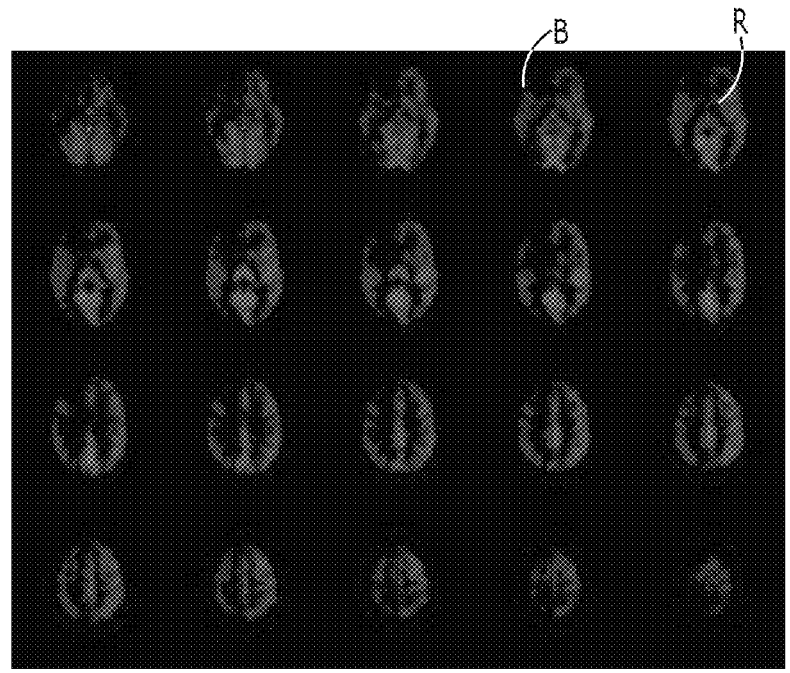
FIGS. 3A and 3B are color maps indicating the location of primary peaks from modulated data in x direction (FIG. 3A) and y direction (FIG. 3B) according to embodiments of the present invention.
Figure 3B:
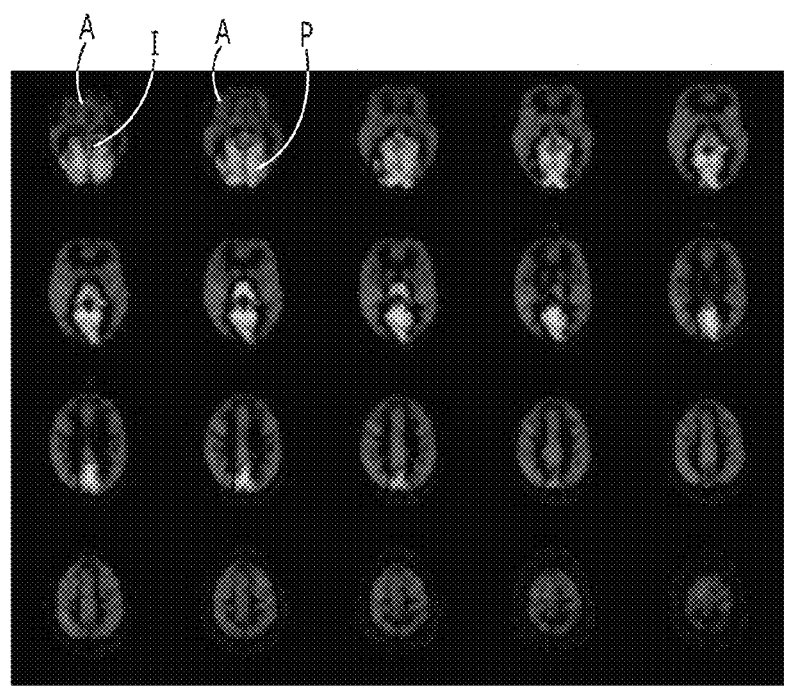

FIGS. 3A/3B show an example of the result of the primary peak detection. FIGS. 3A/3B provide a set of color location maps that indicate the location of primary peaks from modulated data in the X direction (FIG. 3A) and in the y direction (FIG. 3B). In the X direction modulation (FIG. 3A), a blue color "B" represents the source artery location in right and the red color "R" on the other half of the images represents the source artery location in left location maps. In FIG. 3B, the color red means from anterior A and the color yellow means from posterior P (in the top row, no yellow in the bottom row) in the y directional modulation. Other colors may be used to represent the directional and locational information. The brightness indicates the intensity of each voxel, which is propotional to the amount of blood flow to each voxel.

Figure 4:
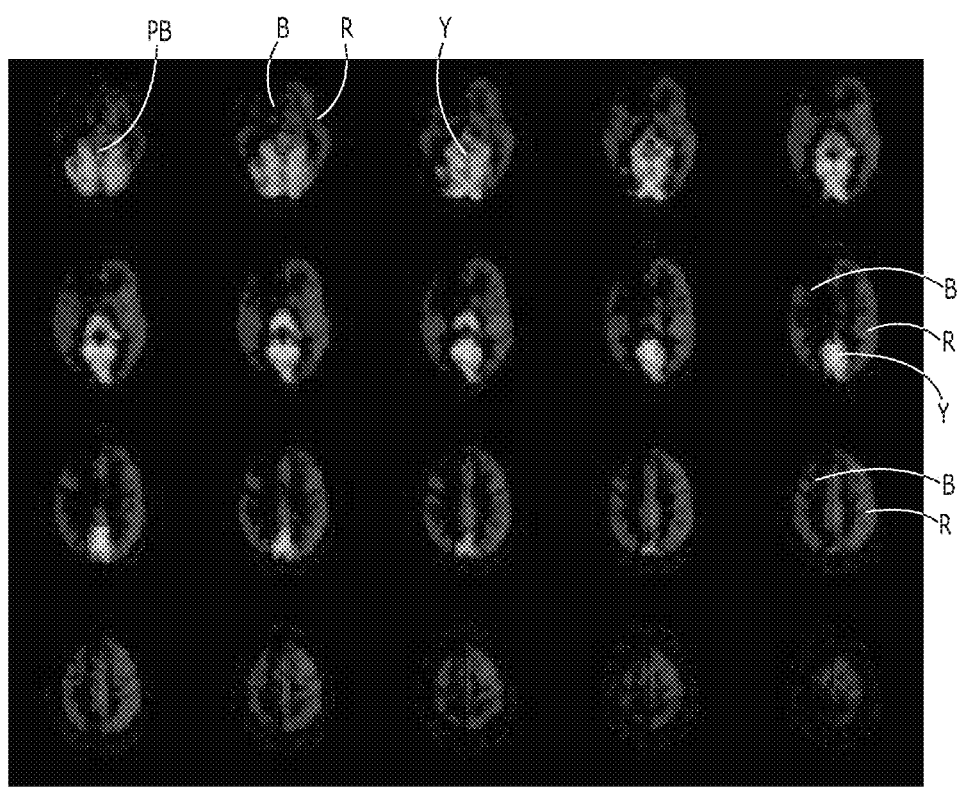
FIG. 4 is a color coded blood flow map generated by combining images shown in FIG. 3A/3B according to embodiments of the present invention.

A combination map of X and Y location information can be provided into 2D space as a 2D color encoded blood flow map as shown in FIG. 4. FIG. 4 combines the images shown in FIGS. 3A/3B so that some images include red, blue and yellow pixels (primarily in the top two rows) and others include only red and blue (e.g., the bottom row). The brighter the voxel/pixel, the greater the amount of blood flow (see the very bright pixel/voxel labeled "PB" in the left most image in the upper row of images). The color coded maps can indicate a respective feeding artery per voxel in unique colors. For example, a right internal carotid artery in blue, a left internal carotid artery in red, a right vertebral artery in cyan, and a left vertebral artery in yellow. However, other colors can be used for one or more of the feeding arteries of interest.

When the acquisition and processing are performed in two orthogonal directions, such as physical X and Y axes, the vessel location in 2D space is estimated by coordinating the location in X and Y into 2D space. The example shown in FIG. 4 represents the location of the artery in 2D space. Here, the signal in blue B is from a source in the upper right (right internal carotid artery), the signal in red R is from a source in the upper left (left internal carotid artery), and the signal in yellow Y is from a lower left direction (left vertebral artery).

The example shown in FIGS. 2-4 used a tagging plane where all carotid and vertebral arteries separated each other in X or Y to demonstrate that two one dimensional encoding procedures are capable of localizing the feeding arteries in a 2D tagging plane. The detection FOV was set at the gradient center and localization parameters in X and Y directions include: 9 cm & 6.6 cm $fov_{det}$, using 15 & 11 encoding steps (with steps 7 & 5 skipped), for a 6 mm & 6 mm resolution. A total of 56 repetitions (4 sec TR) were acquired (2(tag/control pair)×2(real/imaginary)×(8 steps in x+6 steps in y)). The MR scan time for the Fourier encoding was under 5 minutes, at 3 minutes, 42 seconds.

Thus, embodiments of the invention can generate panels of 2D color encoded blood flow maps of a subject using separate and/or combined A/P and R/L (X/Y) encoding according to embodiments of the present invention.

Figure 5A:
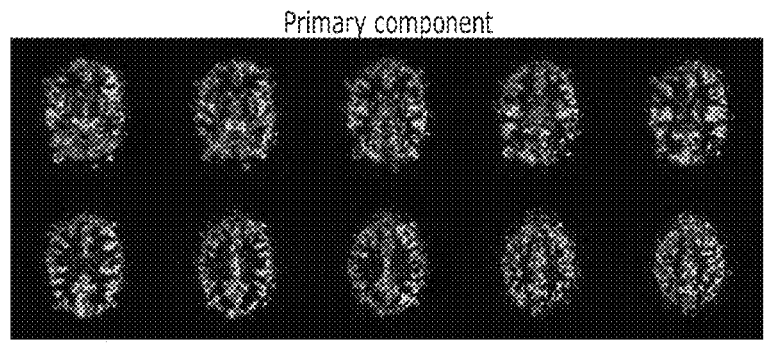
FIG. 5A illustrates images of primary components with location and source information according to embodiments of the present invention.
Figure 5B:
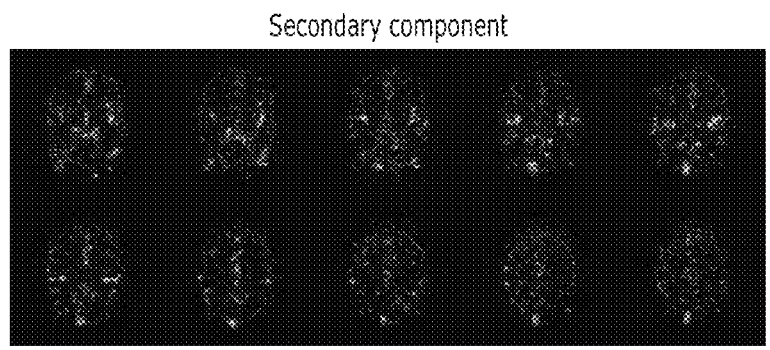
FIG. 5B illustrates images with secondary contributions from feeding arteries according to embodiments of the present invention.
Figure 5C:
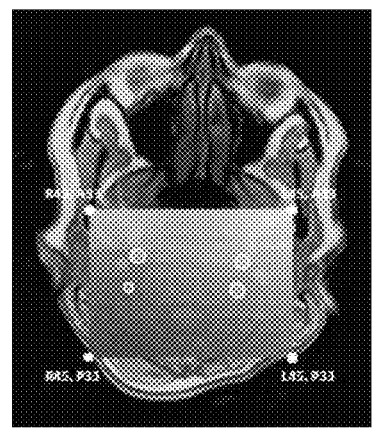
FIG. 5C is a color map overlaid on a time of flight image with the white circles in the corners indicating the main arteries at the tagging plane according to embodiments of the present invention.

The magnitude and source location of ASL signal from the primary peak in the brain are shown in FIG. 5A. The vascular territories were well defined without the use of complicated clustering algorithms. The color of each voxel represents the source of artery (shown in FIG. 5C). The second peak information forming a secondary component in the brain is shown in FIG. 5B. The second component appears to be mostly vascular pulsations and no distinct secondary components due to mixing were presented in this subject.

Figure 6:
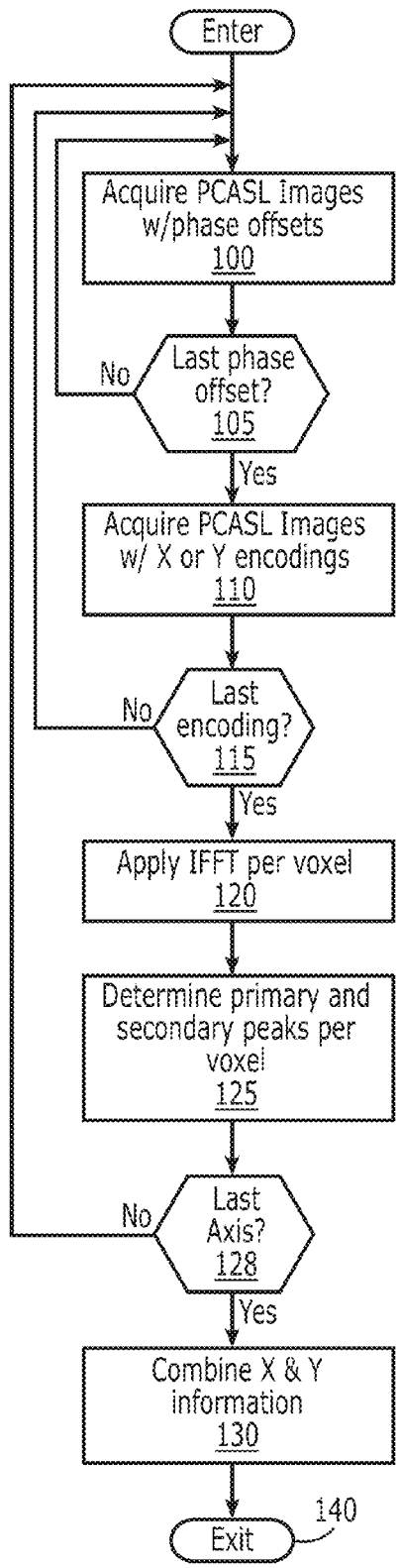
FIG. 6 is a flow chart of operations that can be used for vascular territory mapping according to embodiments of the present invention.

FIG. 6 is a flow chart of exemplary operations that can be carried out according to embodiments of the present invention. As shown, the data processing can include acquiring PCASL images with varying phase offsets (box 100). If the number of phase offsets is less than that desired, e.g., it is not the last phase offset, the acquiring can be repeated (box 105). Once the PCASL images with phase offsets have been acquired, PCASL images can be acquired with X and/or Y directional encodings (typically both, and in any order) (box 110). Then an Inverse Fourier Transform (IFFT), typically a 1-dimensional IFFT, can be applied per voxel (box 120). Primary and secondary peaks per voxel of the IFFT (reconstructed) images can be (electronically/programmatically) determined (box 125). This can be repeated for each of images along both the X axis and the Y axis (block 128). Color encoded blood flow maps that combine the location of primary peaks with X and Y encoded data can be generated (block 130). The color maps can use defined colors to represent location of source arteries and a quantitative or qualitative of blood flow based on pixel/voxel brightness. The color maps may be 2-D color maps that show respective feeding arteries per voxel in unique colors. For example, right internal carotid artery in blue, left internal carotid artery in red, and right vertebral artery in cyan, and left vertebral artery in yellow.

VE-ASL using Fourier encoding offers quantitative vascular territory mapping without the knowledge of accurate locations of feeding arteries or complicated post processing algorithm. In addition, the method is resistant to, if not immune to, phase errors due to resonance offsets, which may cause severe tagging efficiency loss in patients with carotid stents or aneurysm clips. While the experiment had minimum planning, the size of the detection FOV should typically be larger than any distance between the two main arteries to prevent aliasing and there is a trade-off between the size of the detection FOV and the detection resolution.

The MRI signal acquisition can be carried out without requiring the use of an administered contrast agent. The vascular color-coded tissue map can be used to identify functional changes in vascular distributions, as well as quantitative measures of blood flow per voxel. This information can be useful for individualized surgical planning and may be more predictive of a resultant stroke than velocity information from ultrasound or measures of ICA luminal diameter.

Fourier encoded ASL is an elegant solution offering quantitative vascular territory mapping without the need for a priori knowledge or manual delineation of the locations of feeding arteries. In addition, the method is believed to be substantially, if not totally, immune to phase errors due to resonance offsets, which may cause severe loss of tagging efficiency, especially in patients with carotid stents or aneurysm clips. This method is also capable of resolving multiple sources feeding blood to a single voxel.

Embodiments of the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (asics), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the present invention are described herein, in part, with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the figures may occur out of the order noted in the figures. For example, two blocks shown in succession may in fact be executed substantially concurrently or the blocks may sometimes be executed in the reverse order or two or more blocks may be combined, or a block divided and performed separately, depending upon the functionality involved.

Figure 7A:
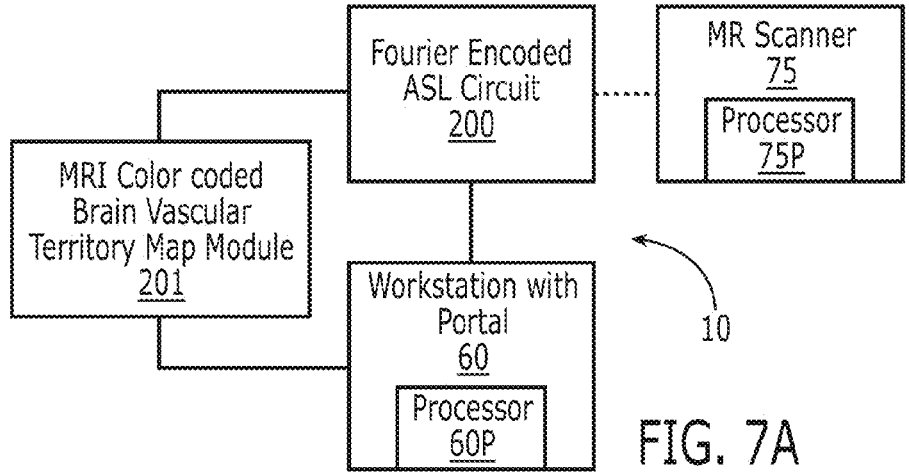
FIGS. 7A-7C are schematic illustrations of systems and circuits that can be configured to provide the Fourier encoded ASL according to embodiments of the present invention.
Figure 7B:
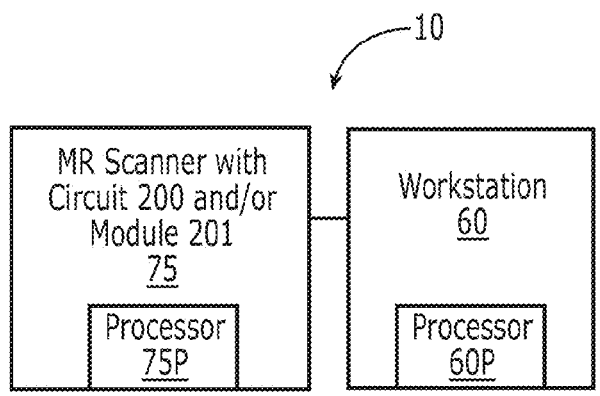
Figure 7C:
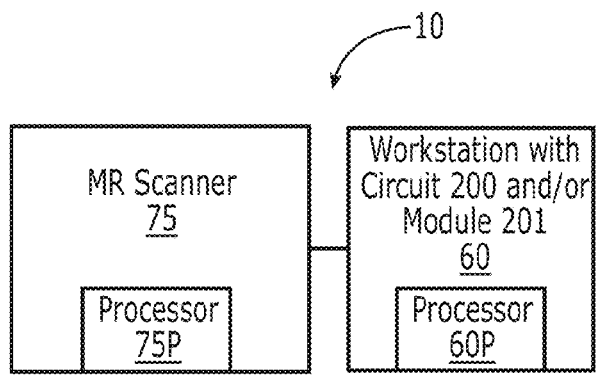

FIGS. 7A-7C illustrate exemplary image processing systems 10 with a Fourier encoded ASL circuit 200 and/or MRI color coded Brain vascular territory map module 201. The systems can be configured to automatically generate color vascular territory maps using rapid (e.g., under 5 minutes of active scanning) brain scans without requiring manual input for identification of arteries to carry out the image processing. The workstation and/or Scanner can each include at least one processor 60P, 75P, respectively, that can be configured to carry out all or part of the image analysis and image acquisition. The image analysis can be performed post-acquisition in a device separate from the Scanner used to acquire the image data.

FIG. 7A illustrates that the system 10 can include at least one workstation 60 that has an optional computer portal for accessing the module 201 and/or circuit 200. The module 201 can be held on a remote server accessible via a LAN, WAN, SAN or Internet. The workstation 60 can communicate with patient image data which may be held in a remote or local server, in the Scanner 75 or other electronically accessible database or repository. The workstation 60 can include a display with a GUI (graphic user input) and the access portal. The workstation can access the data sets via a relatively broadband high speed connection using, for example, a LAN or may be remote and/or may have lesser bandwidth and/or speed, and for example, may access the data sets via a WAN and/or the Internet. Firewalls may be provided as appropriate for security.

FIG. 7B illustrates that the circuit 200 and module 201 can be included in the MR Scanner 75 which can communicate with a workstation 60. The module 201 and/or circuit 200 can be integrated into the control cabinet of the MR Scanner with image processing or scan sequence control circuitry. FIG. 7C illustrates that the circuit 200 and/or module 201 can be integrated into one or more local or remote workstations 60 that communicates with the Scanner 75. Although not shown, parts of the circuit or module can be held on both the Scanner 75 and one or more workstations 60, which can be remote or local. The module and circuit can be combined or separated into further components.

The circuits and modules 200, 201 and methods of embodiments of the application can provide vascular territory mapping using non-contrast enhanced (NCE-) MRA methods. The proportions of blood flow indicated in the images can be scaled to reflect qualitative measures of blood flow, but preferably quantitative measures of blood flow.

Embodiments of the invention can be used clinically for various conditions including, screening, and analysis of impairments, disease and the like including, but not limited to, carotid artery stenosis. For the latter, it is expected that the degree of carotid stenosis can be identified based on a quantified collateral flow from the vascular territory mapping methods described herein.

The Fourier encoded ASL can be used to generate vessel territory maps without requiring operator intervention to identify vessel locations or complicated post-processing algorithms. Fourier encoded ASL is an elegant solution offering quantitative vascular territory mapping without the need for a priori knowledge or manual delineation of the locations of feeding arteries. In addition, the method is immune to phase errors due to resonance offsets, which may cause severe loss of tagging efficiency, especially in patients with carotid stents or aneurysm clips. This method is also capable of resolving multiple sources feeding blood to a single voxel.

Figure 8:
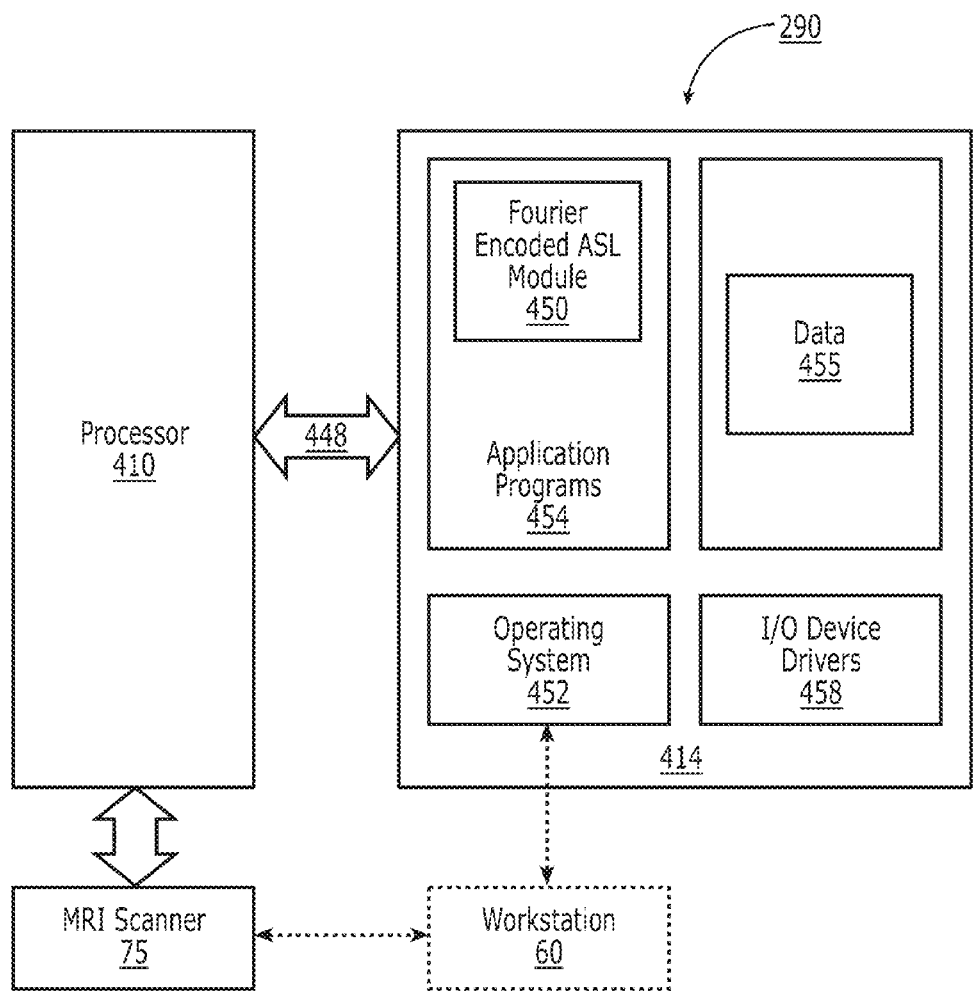
FIG. 8 is a block diagram of a data processing circuit according to embodiments of the present invention.

FIG. 8 is a schematic illustration of a circuit or data processing system 290. The system 290 can be used with any of the systems 10 and provide all or part of the circuit 200 and/or module 201. The circuits and/or data processing systems 290 data processing systems may be incorporated in a digital signal processor in any suitable device or devices. As shown in FIG. 8, the processor 410 can communicate with an MRI scanner 75 and with memory 414 via an address/data bus 448. The processor 410 can be any commercially available or custom microprocessor. The memory 414 is representative of the overall hierarchy of memory devices containing the software and data used to implement the functionality of the data processing system. The memory 414 can include, but is not limited to, the following types of devices: cache, ROM, PROM, EPROM, EEPROM, flash memory, SRAM, and DRAM.

FIG. 8 illustrates that the memory 414 may include several categories of software and data used in the data processing system: the operating system 452; the application programs 454; the input/output (I/O) device drivers 458; and data 455. The data 455 can include patient-specific MRI image (slice) data. FIG. 8 also illustrates the application programs 454 can include an image reconstruction Module 450 that can include a Fourier encoded ASL module that can generate color coded and/or encoded vascular maps of the brain.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000, windowsxp or other Windows versions from Microsoft Corporation, Redmond, Wash., Unix or Linux or freebsd, Palm OS from Palm, Inc., Mac OS from Apple Computer, labview, or proprietary operating systems. The I/O device drivers 458 typically include software routines accessed through the operating system 452 by the application programs 454 to communicate with devices such as I/O data port(s), data storage 455 and certain memory 414 components. The application programs 454 are illustrative of the programs that implement the various features of the data (image) processing system and can include at least one application, which supports operations according to embodiments of the present invention. Finally, the data 455 represents the static and dynamic data used by the application programs 454, the operating system 452, the I/O device drivers 458, and other software programs that may reside in the memory 414.

While the present invention is illustrated, for example, with reference to the Module 450 being an application program in FIG. 8, as will be appreciated by those of skill in the art, other configurations may also be utilized while still benefiting from the teachings of the present invention. For example, the Module 450 may also be incorporated into the operating system 452, the I/O device drivers 458 or other such logical division of the data processing system. Thus, the present invention should not be construed as limited to the configuration of FIG. 8 which is intended to encompass any configuration capable of carrying out the operations described herein. Further, Module 450 can communicate with or be incorporated totally or partially in other components, such as an MRI scanner 75, interface/gateway or workstation 60.

The I/O data port can be used to transfer information between the data processing system, the workstation, the MRI scanner, the interface/gateway and another computer system or a network (e.g., the Internet) or to other devices or circuits controlled by the processor. These components may be conventional components such as those used in many conventional data processing systems, which may be configured in accordance with the present invention to operate as described herein.

Embodiments of the invention provide a novel vascular territory mapping method requiring minimal operator intervention and simple post-processing routines that are suitable for clinical implementation. In addition, the methods can provide voxel-wise quantitative mapping of blood flow in the brain.

Figure 9:
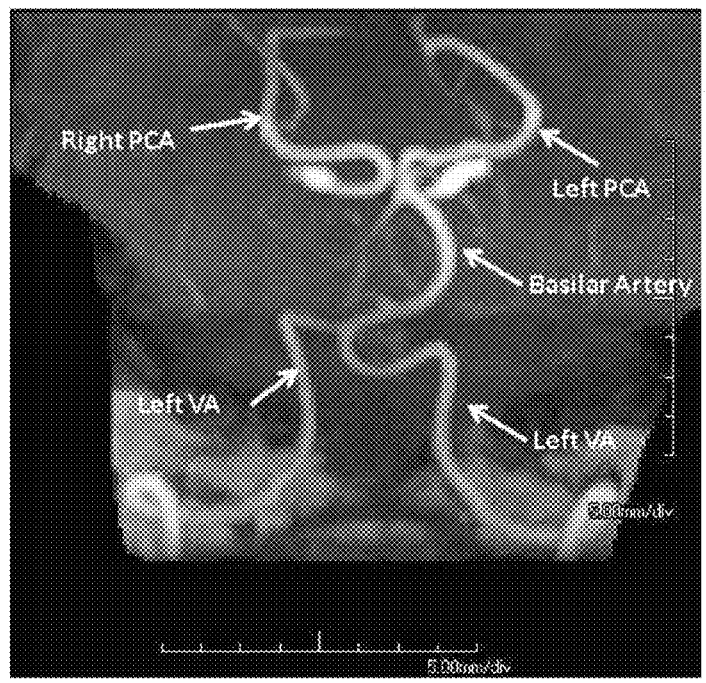
FIG. 9 is an MR (time of flight) angiogram of a patient having an abnormal distribution of arteries.
Figure 10:
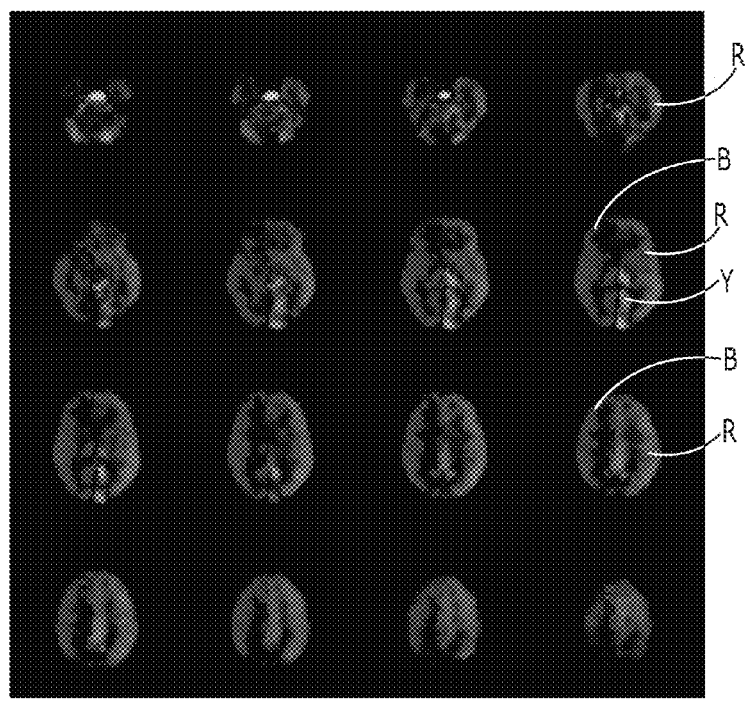
FIG. 10 is a 2-D color map of the patient having the condition shown in FIG. 9 according to embodiments of the present invention.

FIG. 9 is an image of a patient angiogram obtained by a time-of flight MR angiogram method. FIG. 10 is a 2D color encoded map of the patient shown in FIG. 9. This patient has an abnormal distribution of arteries called "fetal origin." The patient's right posterior cerebral artery (PCA) takes blood from the right carotid artery, not from basilar artery. FIG. 10 illustrates that embodiments of the application can be useful to identify abnormalities and not just carotid stenosis.

Figure 11A:
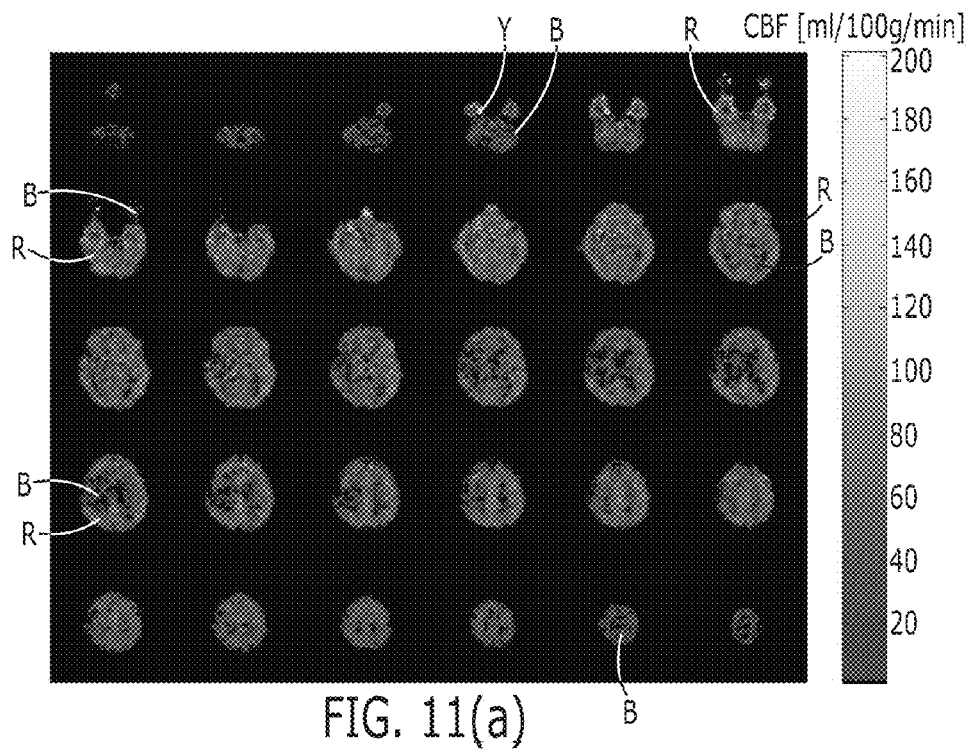
FIGS. 11A and 11B are images of a patient with a history of benign tumor and shows abnormal vascular supply.
Figure 11B:
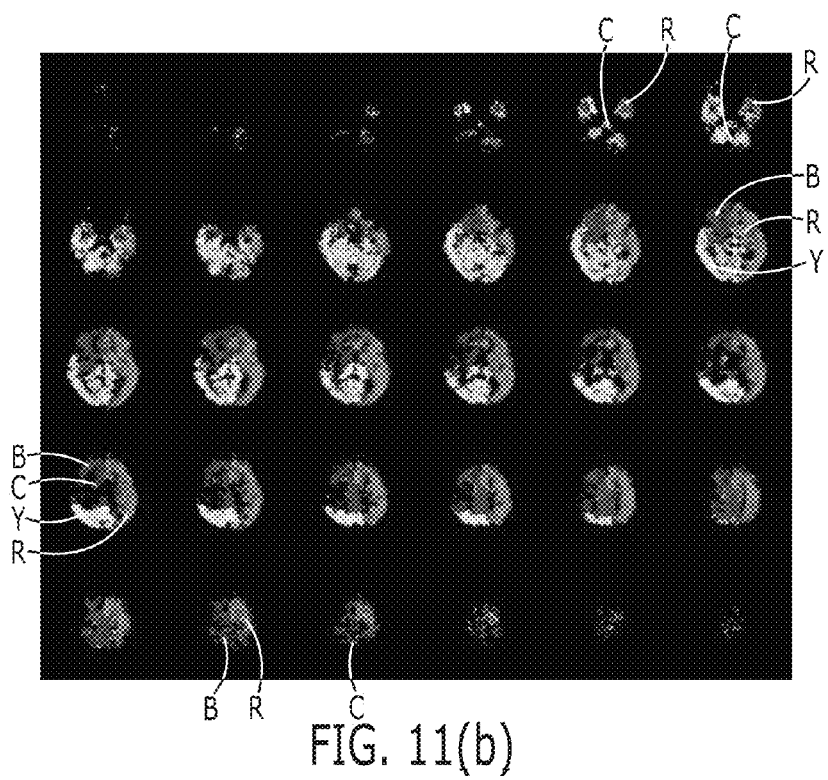

FIGS. 11A and 11B are images of a patient who has a history of benign tumor and shows abnormal vascular supply. FIGS. 11A and 11B are cerebral blood flow maps and 2D color encoded vascular territory maps, respectively. FIG. 11A is in a physiological unit, Cerebral Blood Flow ("CBF") map, (ml/100 g/min) and FIG. 11B shows a vascular territory map overlaid on the CBF map. In FIG. 11B, the color represents the source of the blood (blue: right internal carotid artery, red: left internal carotid artery, cyan: right vertebral artery, and yellow: left vertebral artery). The vascular territory map of FIG. 11B represents that left vertebral artery dominantly contributes the blood supply in the areas of posterior cerebral arteries and right middle cerebral artery.

Figures 12A, 12B, 12C:
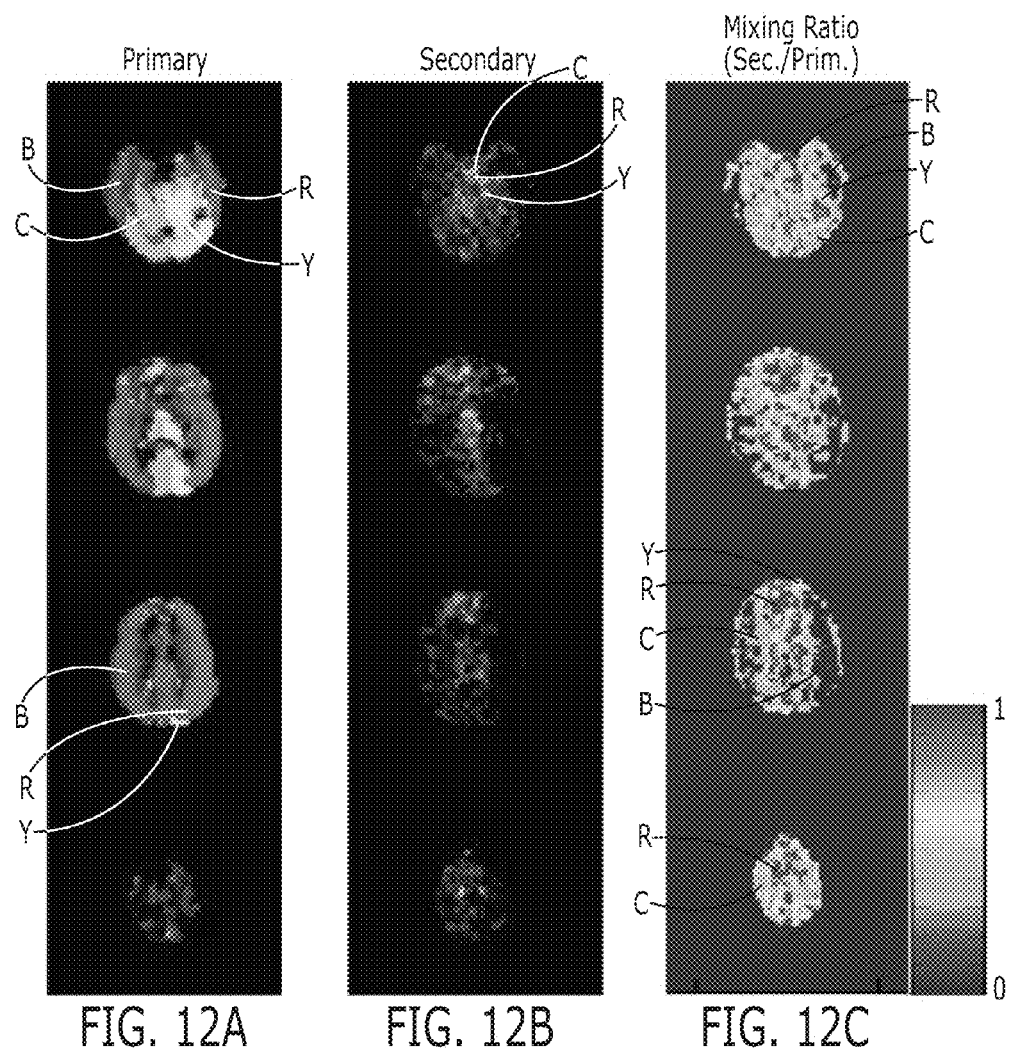
FIGS. 12A-12C are respective columns of a series of 2-D blood flow maps.

FIG. 12C shows a series of 2-D images of blood mixing ratios (top to bottom) that combine blood flow data from the secondary (FIG. 12B) and primary (FIG. 12A) encoded blood flow maps (secondary/primary) according to embodiments of the present invention.

FIGS. 12A-2C is an example of primary and secondary components measured by the Fourier encoding method contemplated by embodiments of the present invention. The brightness of an image indicates the amount of blood flow and the color represents the source of the blood (blue: right internal carotid artery, red: left internal carotid artery, cyan: right vertebral artery, and yellow: left vertebral artery). The column of FIG. 12A shows the primary component and the column of FIG. 12B indicates the secondary component. Thus, FIG. 12C shows images color coded to represent the ratio of the secondary and the primary component in which higher values means larger amounts of blood from two arteries. The posterior circulation area has a higher mixing ratio since the blood from two vertebral arteries is mixed together when it passes through basilar artery. The anterior circulation has also a higher mixing ratio indicating the blood from two internal carotid arteries is mixed together when it goes through anterior cerebral arteries.

The column shown by FIG. 12C represents the ratio of the secondary and the primary component in which higher value means larger amount of blood from two arteries. The areas of anterior cerebral arteries and posterior cerebral arteries have a higher mixing ratio, which indicates the blood from two internal carotid arteries is mixed together when it goes through anterior cerebral arteries and the blood from two vertebral arteries is mixed together when it passes through basilar artery. The mixing ratio images can be shown separate from the secondary or primary images for clinical use or each may be selectively displayed. The sets of images can be shown in other groupings, e.g., rows or selectable windows.

Blood flow quantification can be in color scale, from "0" (blue) to "1" (red) with intermediate values shown (in terms of increasing blood flow) from blue to green to yellow to orange as the value approaches the full scale "red" or "1" value of the mixing ratio. Typical cerebral blood flow rates are between 0-200 ml/100 g/min. The reverse ratio calculation may also be used. Different flow scales and/or colors for the scale may also be used.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A method of mapping brain vascular perfusion using MRI comprising:
   acquiring a set of multiple pseudo-continuous arterial spin label (PCASL) images with varying phase offsets,
   acquiring a set of pseudo-continuous arterial spin label (PCASL) images with X directional encoding;
   acquiring a set of PCASL images with Y directional encoding; electronically generating complex signals per voxel; then
   electronically applying a one-dimensional inverse Fourier transform (IFT) per voxel of the X and Y encoded images; then
   electronically evaluating each voxel of the X and Y encoded images using the applied one-dimensional IFT to determine X, Y locations of primary and secondary voxel intensity peaks to localize feeding arteries, wherein the primary voxel intensity peak is a highest voxel intensity and the secondary voxel intensity peak is a second highest voxel intensity; and
   generating at least one two-dimensional color blood flow map that combines X and Y encoded primary and secondary peak data to visually indicate anterior/posterior and right/left directional components of respective feeding arteries using defined colors, the map further configured to visually indicate an amount of blood flow associated with each voxel using brightness of intensity, with increased brightness associated with increased blood flow.

2. The method of claim 1, wherein the acquiring the PCASL encoded images is carried out by first acquiring PCASL images using a sinusoidal modulation with four phase offsets to form real and imaginary parts of a complex modulation and using gradients that are the same in X or Y directions across an entire tagging period, and wherein the applied IFT can resolve multiple feeding vessel locations in the corresponding X or Y directions.

3. The method of claim 1, wherein the at least one color blood flow map is overlaid onto a time of flight image on a display and the color map includes visual indicia comprising circles that identifies each location of four arteries at a tagging plane.

4. The method of claim 1, wherein the color map indicates the associated feeding artery per voxel in unique colors.

5. The method of claim 4, wherein a right internal carotid artery is shown in blue, a left internal carotid artery is shown in red, a right vertebral artery is shown in cyan, and a left vertebral artery is shown in yellow.

6. The method of claim 1, wherein the generating the at least one color blood flow image is carried out to generate a plurality of image slices that are concurrently presented in a panel or window on a display, and wherein the acquired images are non-contrast enhanced images obtained with a scan time of about 5 minutes or less.

7. The method of claim 2, wherein the sinusoidal modulation is carried out so that the sinusoidal modulation is complex with an imaginary component of the modulated signal that is 90 degrees phase offset, wherein the four phase offsets (Δθ) are provided as: a real pair at 0°/180° and an imaginary pair at 90°/270°, wherein the gradients are carried out with gradient steps: $n/(\gamma FOV_{det})$ n: $-(N-1)/2, \ldots, 0, \ldots, (N-1)/2$, where γ is a gyromagnetic ratio, $FOV_{det}$ is a predefined detection FOV set at a tagging plane, and N is the number of encoding steps in a direction which defines a resolution of vessel localization in the color map.

8. The method of claim 7, wherein to reduce gradient steps while preserving detection resolution, positive or negative gradient steps are skipped and synthesized by taking a complex conjugate of mirrored steps based on Hermitian symmetry after removing a phase component of DC signal from all acquired data which is acquired without gradient encoding.

9. The method of claim 1, further comprising displaying the at least one map on a clinician workstation.

10. The method of claim 1, wherein the acquiring steps are carried out using a processor associated with an MR Scanner.

11. The method of claim 1, further comprising generating a series of mixing ratio color blood flow maps using a ratio of encoded primary and secondary peak data.

12. The method of claim 1, wherein the IFT is applied per voxel after acquiring the PCASL images with phase offsets with respective X or Y encoding and before generating the color blood flow maps, and wherein the color blood flow maps are generated using two-dimensional locations of primary voxel intensity peaks identified by the applied IFT to resolve feeding artery location.

13. The method of claim 12, wherein the generating step can identify multiple source arteries that feed blood to a single voxel using only the acquired PCASL images and the applied 1-D IFT.

14. The method of claim 1, wherein the applied one-dimensional IFT converts a modulated complex signal into projected ASL signals onto the X or Y encoding direction to localize the feeding arteries.

15. The method of claim 1, wherein the method further comprises electronically identifying locations of the primary voxel intensity peak and the secondary voxel intensity peak and correlating to a physical location in 2D or 3D space to represent an amount of blood flow and location of a primary perfusion component with peak locations of an individual voxel in two orthogonal directions to estimate 2D location of a feeding artery for the color blood flow map, and wherein the second highest intensity peak can identify when mixing due to multiple arterial sources is present.

16. An image processing circuit configured to carry out claim 1.

17. A data processing circuit comprising at least one processor configured to: (i) acquire a set of multiple pseudo-continuous arterial spin label (PCASL) images with varying phase offsets, (ii) acquire a set of non-contrast enhanced pseudo-continuous arterial spin label (PCASL) images with X directional encoding; (iii) acquire a set of PCASL images with Y directional encoding; (iv) apply a one-dimensional inverse Fourier transform (IFT) per voxel of the X and Y encoded images; then (v) evaluate each voxel of the X and Y encoded images to determine two-dimensional locations of primary and secondary voxel intensity peaks based on the IFT, wherein the primary voxel intensity peak is a highest voxel intensity and the secondary voxel intensity peak is a second highest voxel intensity; and then (vi) generate at least one two-dimensional color blood flow map that combines X and Y encoded primary and secondary peak data to visually indicate (a) anterior/posterior and right/left directional components of respective feeding arteries using defined colors and (b) an amount of blood flow associated with each voxel using brightness, with increased brightness associated with increased blood flow.

18. The data processing circuit of claim 17, wherein the circuit identifies locations of the primary voxel intensity peak and the secondary voxel intensity peak and correlates a physical location in 2D or 3D space to represent an amount of blood flow and location of a primary perfusion component with peak locations of an individual voxel in two orthogonal directions to estimate a 2D location of a feeding artery for the color blood flow map, and wherein a second highest intensity peak can identify when mixing due to multiple arterial sources is present.

19. A computer program product comprising non-transitory computer readable storage medium having a non-transitory computer readable program code embodied in the medium, the computer-readable program code configured to perform by at least one processor the following steps:

acquiring a set of multiple pseudo-continuous arterial spin label (PCASL) images with varying phase offsets, acquiring a set of pseudo-continuous arterial spin label (PCASL) images with X directional encoding;

acquiring a set of PCASL images with Y directional encoding;

electronically generating complex signals per voxel; then applying a one-dimensional inverse Fourier transform (IFT) per voxel of X and Y encoded pseudo-continuous arterial spin label images; then evaluating each voxel of the X and Y encoded images to determine two-dimensional locations of primary and secondary voxel intensity peaks associated with feeding arteries based on the applied IFT, wherein the primary voxel intensity peak is a highest voxel intensity and the secondary voxel intensity peak is a second highest voxel intensity; and generating at least one two-dimensional color blood flow map that combines X and Y encoded primary and secondary peak data to visually indicate (i) anterior/posterior and right/left directional components of respective feeding arteries using defined colors and (ii) an amount of blood flow associated with each voxel using brightness, with increased brightness associated with increased blood flow.

20. The computer program product of claim 19, wherein the computer-readable program code is further configured to perform by the at least one processor the following step of: forming real and imaginary parts of a complex modulation.

21. The computer program product of claim 19, wherein the computer-readable program code that evaluates each voxel of the X and Y encoded images to determine the two-dimensional locations of the primary and secondary voxel intensity peaks associated with feeding arteries based on the applied IFT is configured to:

apply the one-dimensional IFT to convert a modulated complex signal into projected arterial spin labeling (ASL) signals onto the X or Y encoding direction to localize the feeding arteries, wherein the computer readable program code identifies locations the primary voxel intensity peak and the secondary voxel intensity peak and correlates a physical location in 2D or 3D space to represent an amount of blood flow and location of a primary perfusion component with peak locations of an individual voxel in two orthogonal directions to estimate a 2D location of a feeding artery for the color blood flow map, and wherein presence of the second highest intensity peak identifies when mixing due to multiple arterial sources is present.

22. A clinician workstation comprising:
at least one display; and
at least one processor configured to: (i) acquire a set of multiple pseudo-continuous arterial spin label (PCASL) images with varying phase offsets, (ii) acquire a set of non-contrast enhanced pseudo-continuous arterial spin label (PCASL) images with X directional encoding; (iii) acquire a set of PCASL images with Y directional encoding; (iv) apply a one-dimensional inverse Fourier transform (IFT) per voxel of the X and Y encoded images; then (v) evaluate each voxel of the X and Y encoded images to determine two-dimensional locations of primary and secondary voxel intensity peaks based on the IFT, wherein the primary voxel intensity peak is a highest voxel intensity and the secondary voxel intensity peak is a second highest voxel intensity; and then (vi) generate at least one two-dimensional color blood flow map that combines X and Y encoded primary and secondary peak data to visually indicate (a) anterior/posterior and right/left directional components of respective feeding arteries using defined colors and (b) an amount of blood flow associated with each voxel using brightness, with increased brightness associated with increased blood flow;
the at least one processor in communication with the at least one display configured to generate at least one two-dimensional color blood flow map that combines X and Y encoded primary and secondary voxel intensity peak data of 1-dimensional IFT images that identifies X, Y coordinate locations of feeding arteries to visually indicate (i) anterior/posterior and right/left directional components of respective feeding arteries using defined colors and (ii) a measure of blood flow associated with each voxel using brightness, with increased brightness associated with increased blood flow.

23. The workstation of claim 22, wherein the color map indicates a respective associated feeding artery per voxel in unique color.

24. The workstation of claim 23, wherein the unique colors include blue for a right internal carotid artery, red for a left internal carotid artery, cyan for a right vertebral artery, and yellow for a left vertebral artery.

25. The workstation of claim 22, wherein the at least one processor is configured to generate at least one two-dimensional color map using a defined ratio of encoded primary and secondary peak data.

26. The workstation of claim 22, wherein the processor is configured to apply the one-dimensional IFT to convert a modulated complex signal into projected arterial spin labeling (ASL) signals onto the X or Y encoding direction to localize the feeding arteries, wherein the circuit identifies locations of the primary voxel intensity peak and the secondary voxel intensity peak and correlates a physical location in 2D or 3D space to represent an amount of blood flow and location of a primary perfusion component with peak locations of an individual voxel in two orthogonal directions to estimate a 2D location of a feeding artery for the color blood flow map, and wherein detection of the second highest intensity peak identifies when mixing due to multiple arterial sources is present.

27. The workstation of claim 22, wherein the at least one processor is configured to generate a series of mixing-ratio color blood flow maps using a ratio of the encoded primary and secondary peak data.

28. An MR scanner comprising:
a high-field magnet; and
at least one processor configured to: (i) acquire a set of multiple pseudo-continuous arterial spin label (PCASL) images with varying phase offsets; (ii) acquire a set of pseudo-continuous arterial spin label (PCASL) images with X directional encoding; (iii) acquire a set of PCASL images with Y directional encoding; (iv) apply an Inverse Fourier Transform (IFT) per voxel of the X and Y encoded PCASL images to identify primary and secondary voxel peak intensity locations associated with feeding arteries in two dimensions, wherein the primary voxel intensity peak is a highest voxel intensity and the secondary voxel intensity peak is a second highest voxel intensity; and (v) generate at least one two-dimensional color blood flow map using the IFT identified locations of the primary and secondary voxel intensity peaks to visually indicate anterior/posterior and right/left directional components of respective feeding arteries using defined colors.

29. The MR Scanner of claim 28, wherein the at least one processor is configured to first acquire PCASL images using a sinusoidal modulation with four phase offsets to form real and imaginary parts of a complex modulation and use gradients that are the same in X and Y directions across an entire tagging period,
wherein the sinusoidal modulation is carried out so that the sinusoidal modulation is complex, wherein the four phase offsets (Δθ) are provided as a real pair at 0°/180° and an imaginary pair at 90°/270°,
wherein the gradients are carried out with gradient steps: $n/(\gamma FOV_{det})$ n: $-(N-1)/2, \ldots, 0, \ldots, (N-1)/2$,
where γ is a gyromagnetic ratio, $FOV_{det}$ is a predefined detection FOV set at a tagging plane, and N is the number of encoding steps in a direction which defines a resolution of vessel localization in the color map.

30. The MR Scanner of claim 28, wherein the at least one processor is configured to apply the one-dimensional IFT to convert a modulated complex signal into projected arterial spin labeling (ASL) signals onto the X or Y encoding direction to localize the feeding arteries, wherein the at least one processor identifies locations of the primary voxel intensity peak and the secondary voxel intensity peak and correlates a physical location in 2D or 3D space to represent an amount of blood flow and location of a primary perfusion component with peak locations of an individual voxel in two orthogonal directions to estimate a 2D location of a feeding artery for the color blood flow map, and wherein detection of the second highest intensity peak identifies when mixing due to multiple arterial sources is present.

* * * * *